US012629112B2

(12) United States Patent
Sommer et al.

(10) Patent No.: US 12,629,112 B2
(45) Date of Patent: May 19, 2026

(54) MEDICAL IMAGE ACQUISITION UNIT ASSISTANCE APPARATUS

(71) Applicant: KONINKLIJKE PHILIPS N.V., Eindhoven (NL)

(72) Inventors: Karsten Sommer, Hamburg (DE); Sascha Krueger, Norderstedt (DE); Joerg Sabczynski, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 18/726,442

(22) PCT Filed: Jan. 9, 2023

(86) PCT No.: PCT/EP2023/050302
§ 371 (c)(1),
(2) Date: Jul. 3, 2024

(87) PCT Pub. No.: WO2023/135074
PCT Pub. Date: Jul. 20, 2023

(65) Prior Publication Data
US 2025/0064411 A1 Feb. 27, 2025

(30) Foreign Application Priority Data
Jan. 14, 2022 (EP) .................................... 22151520

(51) Int. Cl.
*A61B 5/00* (2006.01)
*A61B 5/107* (2006.01)
(Continued)

(52) U.S. Cl.
CPC .......... *A61B 6/0407* (2013.01); *A61B 5/1079* (2013.01); *G06T 7/50* (2017.01);
(Continued)

(58) Field of Classification Search
CPC ....... A61B 6/0407; A61B 5/1079; G06T 7/20; G06T 7/60; G06T 7/70
See application file for complete search history.

(56) References Cited

U.S. PATENT DOCUMENTS

| | | |
|---|---|---|
| 2018/0078034 A1 | 3/2018 | Savall et al. |
| 2019/0150874 A1* | 5/2019 | Kagermeier ........... A61B 6/547 |
| 2019/0321126 A1* | 10/2019 | Otto ...................... A61B 90/37 |

FOREIGN PATENT DOCUMENTS

| | | |
|---|---|---|
| CN | 107616808 A | 1/2018 |
| CN | 111789619 A | 10/2020 |

OTHER PUBLICATIONS

International Search Report and Written Opinion from PCT/EP2023/050302 mailed Mar. 21, 2023.

(Continued)

*Primary Examiner* — Joel F Brutus

(57) ABSTRACT

The present invention relates to a medical image acquisition unit assistance apparatus (10) comprising: at least one camera (20); a processing unit (30); and an output unit (40). The at least one camera is configured to be located in the vicinity of a patient support of a medical image acquisition unit. The at least one camera is configured to acquire at least one data of a human operator standing adjacent to the patient support. The at least one camera is configured to provide the at least one data of the operator to the processing unit. The processing unit is configured to determine a height of the operator, wherein the determination comprises utilization of the at least one data. The output unit is configured to output a signal to adjust a height of the patient support, wherein the adjustment comprises utilization of the height of the operator.

20 Claims, 4 Drawing Sheets

(51) Int. Cl.

| | |
|---|---|
| *A61B 6/04* | (2006.01) |
| *G06T 7/50* | (2017.01) |
| *G06T 7/60* | (2017.01) |
| *G06T 7/70* | (2017.01) |
| *G06V 10/44* | (2022.01) |
| *G16H 30/20* | (2018.01) |

(52) U.S. Cl.
CPC .................. *G06T 7/60* (2013.01); *G06T 7/70* (2017.01); *G06V 10/44* (2022.01); *G16H 30/20* (2018.01)

(56) References Cited

OTHER PUBLICATIONS

Simonyan, K. and Zisserman, A., 2014. Very deep convolutional networks for large-scale image recognition. arXiv preprint arXiv:1409. 1556.

He, K., Zhang, X., Ren, S. and Sun, J., 2016. Deep residual learning for image recognition. In Proceedings of the IEEE conference on computer vision and pattern recognition (pp. 770-778).

Hermans, A., Beyer, L. and Leibe, B., 2017. In defense of the triplet loss for person re-identification. arXiv preprint arXiv:1703.07737.

Radiology Staff in Focus (2019).

* cited by examiner

MEDICAL IMAGE ACQUISITION UNIT ASSISTANCE APPARATUS

CROSS REFERENCE TO RELATED APPLICATIONS

This application is a U.S. national phase application of International Application No. PCT/EP2023/050302 filed on Jan. 9, 2023, which claims the benefit of EP Application Serial No. 22151520.8 filed on Jan. 14, 2022 and is incorporated herein by reference.

FIELD OF THE INVENTION

The present invention relates to a medical image acquisition unit assistance apparatus, a medical image acquisition unit assistance system, a medical image acquisition unit assistance method, as well as to a computer program element and a computer readable medium.

BACKGROUND OF THE INVENTION

Patient preparation is an essential and critical element of the clinical workflow in a medical imaging examinations, for example for MRI, X-ray, CT, attenuation X-ray, PET etc. This is because the time needed to prepare the patient restricts the potential available timeslot for the actual scan. During the exam preparation workflow, the patient support (table) height is typically adjusted multiple times to allow for convenient table preparation as well as to improve patient comfort. This table height adjustment generally has to be performed manually by the operator. This not only prolongs exam preparation time but is particularly cumbersome while carrying a large/heavy object (e.g. anterior coil) with both hands. Furthermore, the daily routine of a medical imaging operator can be both stressful and physically demanding due to the complexity of many required tasks as well as strict time constraints. These problems are exacerbated because at most clinical sites a large number of technicians typically work on the same medical imaging system, and they often have large differences in experience and working style.

There is a need to resolve these issues.

SUMMARY OF THE INVENTION

It would be advantageous to provide improved assistance to operators of medical image acquisition units. The object of the present invention is solved with the subject matter of the independent claims, wherein further embodiments are incorporated in the dependent claims. It should be noted that the following described aspects and examples of the invention apply to the medical image acquisition unit assistance apparatus, the medical image acquisition unit assistance system, the medical image acquisition unit assistance method, and also to the medical imaging method as well as to the computer program element and the computer readable medium.

In a first aspect, there is provided a medical image acquisition unit assistance apparatus comprising:

at least one camera;

a processing unit; and an output unit.

The at least one camera is configured to be located in the vicinity of a patient support of a medical image acquisition unit. The at least one camera is configured to acquire at least one data of a human operator standing adjacent to the patient support. The at least one camera is configured to provide the at least one data of the operator to the processing unit. The processing unit is configured to determine a height of the operator. The determination comprises utilization of the at least one data. The output unit is configured to output a signal to adjust a height of the patient support, wherein the adjustment comprises utilization of the height of the operator.

In this way, the height of a patient support (such as a table) is automatically adjusted to the optimum height for the operator who is preparing a patient on the patient support for an examination by a medical image acquisition unit such as a MRI, X-Ray unit, PET scanner etc. The operator does not need to do this manually, freeing up the operator's time, making for more time efficient and effective examinations.

In an example, the utilization of the at least one data comprises a determination of a location of the operator in the at least one data.

In an example, the determination of the height of the operator comprises a determination of at least one height at the determined location of the operator.

Thus, the at least one camera could be a single camera, such as a time-of-flight based depth and imaging camera, from which the location of the operator can be determined and their height. However, the at least one camera could be two visible light cameras, operating in stereo mode, with imagery from both cameras is analyzed to determine depth information and the location of the operator enabling the operator site to be determined.

In an example, the at least one camera comprises a camera configured to acquire 2D image data, and the at least one data comprises a 2D image. The processing unit is configured to determine the location of at least one body part of the operator in the 2D image.

In an example, the at least one camera comprises a camera configured to acquire depth or distance data, and the at least one data comprises depth or distance data. The processing unit is configured to determine the height of the operator on the basis of the depth or distance data at the determined location of the at least one body part of the operator.

In an example, the at least one body part of the operator comprises the top of the head of the operator and/or the neck of the operator and/or the shoulders of the operator.

In an example, the camera configured to acquire depth or distance data is configured to be located above the patient support.

In an example, the determination of the height of the operator comprises utilization of a known height of the camera configured to acquire depth or distance data above a floor upon which the patient support is located.

In an example, the utilization of the at least one data comprises a determination of an identity of the operator in the at least one data.

In an example, the determination of the height of the operator comprises an extraction of the height of the operator from a database on the basis of the identity of the operator.

In other words, by identifying the operator, the personal details can be extracted from a database, where those personal details include the operator's height, enabling the height of the patient support to be adjusted appropriately.

In an example, the at least one camera comprises a camera configured to acquire 2D image data, and the at least one data comprises a 2D image. The processing unit is configured to determine the identity of the operator comprising image analysis of the 2D image.

In an example, the processing unit is configured to determine at least one workflow support feature relating to operation of the medical image acquisition unit by the operator comprising extraction of the at least one workflow support feature from a database on the basis of the identity of the operator. The output unit is configured to communicate the at least one workflow support feature to the operator.

In this manner, the at least one workflow support feature, such as how to operate the medical image acquisition unit for a particular procedure, can be tailored to the operator. For example, for a junior and/or inexperienced operator, very detailed procedural workflow steps can be provided to the operator enabling them to appropriately carry out the examination. However, for an experienced operator, a much more pared back set of support features can be provided to this operator.

In a second aspect, there is provided a medical image acquisition system comprising:
- a medical image acquisition unit;
- at least one camera;
- a processing unit; and
- an output unit.

The at least one camera is located in the vicinity of a patient support of a medical image acquisition unit. The at least one camera is configured to acquire at least one data of a human operator standing adjacent to the patient support. The at least one camera is configured to provide the at least one data of the operator to the processing unit. The processing unit is configured to determine a height of the operator. The determination comprises utilization of the at least one data. The output unit is configured to output a signal to adjust a height of the patient support, wherein the adjustment comprises utilization of the height of the operator.

In a third aspect, there is provided a medical image acquisition unit assistance method comprising:
- acquiring by at least one camera at least one data of a human operator standing adjacent to a patient support of a medical image acquisition unit;
- providing by the at least one camera the at least one data of the operator to a processing unit;
- determining by the processing unit a height of the operator, wherein the determining comprises utilizing the at least one data; and
- outputting by an output unit a signal to adjust a height of the patient support, wherein the adjustment comprises utilizing the height of the operator.

According to another aspect, there is provided a computer program element controlling one or more of the apparatuses and/or systems as previously described which, if the computer program element is executed by a processor, is adapted to perform the method as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figures 1, 2, 3:
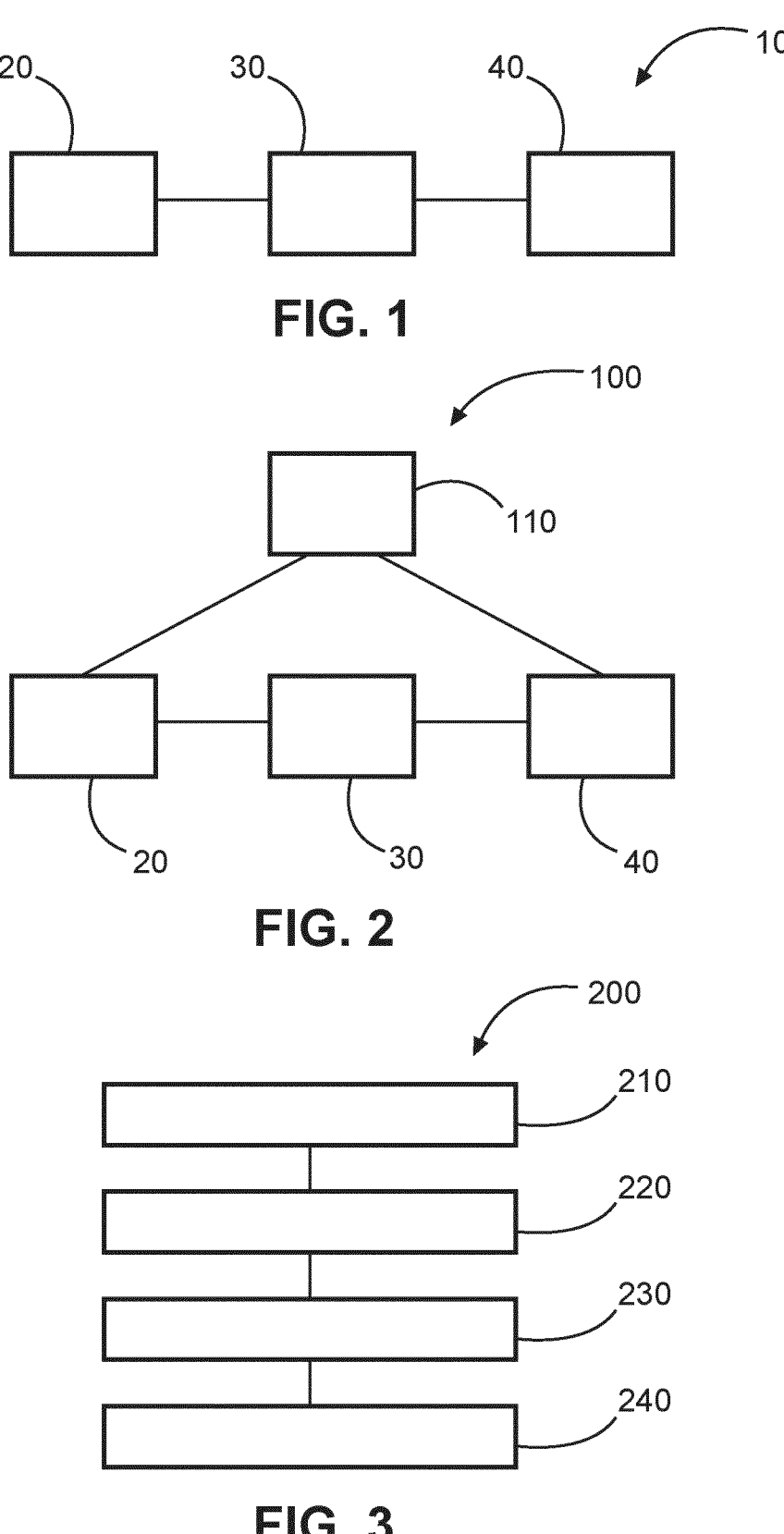
FIG. 1 shows a schematic example of a medical image acquisition unit assistance apparatus.
FIG. 2 shows a schematic example of a medical image acquisition unit assistance system.
FIG. 3 shows a medical image acquisition unit assistance method.

FIG. 1 shows an example of a medical image acquisition unit assistance apparatus 10. The apparatus comprises at least one camera 20, a processing unit 30, and an output unit 40. The at least one camera is configured to be located in the vicinity of a patient support of a medical image acquisition unit. The at least one camera is configured to acquire at least one data of a human operator standing adjacent to the patient support. The at least one camera is configured to provide the at least one data of the operator to the processing unit. The processing unit is configured to determine a height of the operator. The determination comprises utilization of the at least one data. The output unit is configured to output a signal to adjust a height of the patient support, wherein the adjustment comprises utilization of the height of the operator.

The apparatus can, for example, be retrofitted to an imaging system that includes a medical image acquisition unit.

According to an example, the utilization of the at least one data comprises a determination of a location of the operator in the at least one data.

According to an example, the determination of the height of the operator comprises a determination of at least one height at the determined location of the operator.

According to an example, the at least one camera comprises a camera configured to acquire 2D image data, and the at least one data comprises a 2D image. The processing unit can then be configured to determine the location of at least one body part of the operator in the 2D image.

According to an example, the at least one camera comprises a camera 22 configured to acquire depth or distance data, and the at least one data comprises depth or distance data. The processing unit can then be configured to determine the height of the operator on the basis of the depth or distance data at the determined location of the at least one body part of the operator.

According to an example, the at least one body part of the operator comprises the top of the head of the operator and/or the neck of the operator and/or the shoulders of the operator.

According to an example, the camera configured to acquire depth or distance data is configured to be located above the patient support.

According to an example, the determination of the height of the operator comprises utilization of a known height of the camera configured to acquire depth or distance data above a floor upon which the patient support is located.

In an example, the depth or distance data comprises at least one distance between the camera and the at least one body part of the operator.

According to an example, the utilization of the at least one data comprises a determination of an identity of the operator in the at least one data.

According to an example, the determination of the height of the operator comprises an extraction of the height of the operator from a database on the basis of the identity of the operator.

According to an example, the at least one camera comprises a camera (24) configured to acquire 2D image data, and the at least one data comprises a 2D image. The processing unit can then be configured to determine the identity of the operator comprising image analysis of the 2D image.

According to an example, the processing unit is configured to determine at least one workflow support feature relating to operation of the medical image acquisition unit by the operator comprising extraction of the at least one workflow support feature from a database on the basis of the identity of the operator. The output unit is configured to communicate the at least one workflow support feature to the operator.

In an example, the camera configured to acquire 2D image data is configured to be located above the patient support.

FIG. 2 shows an example of a medical image acquisition system 100. The system comprises a medical image acquisition unit 110, at least one camera 20, a processing unit 30, and an output unit 40. The at least one camera is located in the vicinity of a patient support of a medical image acquisition unit. The at least one camera is configured to acquire at least one data of a human operator standing adjacent to the patient support. The at least one camera is configured to provide the at least one data of the operator to the processing unit. The processing unit is configured to determine a height of the operator. The determination comprises utilization of the at least one data. The output unit is configured to output a signal to adjust a height of the patient support, wherein the adjustment comprises utilization of the height of the operator.

In an example, the utilization of the at least one data comprises a determination of a location of the operator in the at least one data.

In an example, the determination of the height of the operator comprises a determination of at least one height at the determined location of the operator.

In an example, the at least one camera comprises a camera configured to acquire 2D image data, and the at least one data comprises a 2D image. The processing unit can then be configured to determine the location of at least one body part of the operator in the 2D image.

In an example, the at least one camera comprises a camera configured to acquire depth or distance data, and the at least one data comprises depth or distance data. The processing unit can then be configured to determine the height of the operator on the basis of the depth or distance data at the determined location of the at least one body part of the operator.

In an example, the at least one body part of the operator comprises the top of the head of the operator and/or the neck of the operator and/or the shoulders of the operator.

In an example, the camera configured to acquire depth or distance data is located above the patient support.

In an example, the determination of the height of the operator comprises utilization of a known height of the camera configured to acquire depth or distance data above a floor upon which the patient support is located.

In an example, the depth or distance data comprises at least one distance between the camera and the at least one body part of the operator.

In an example, the utilization of the at least one data comprises a determination of an identity of the operator in the at least one data.

In an example, the determination of the height of the operator comprises an extraction of the height of the operator from a database on the basis of the identity of the operator.

In an example, the at least one camera comprises a camera configured to acquire 2D image data, and the at least one data comprises a 2D image. The processing unit can then be configured to determine the identity of the operator comprising image analysis of the 2D image.

In an example, the processing unit is configured to determine at least one workflow support feature relating to operation of the medical image acquisition unit by the operator comprising extraction of the at least one workflow support feature from a database on the basis of the identity of the operator. The output unit is configured to communicate the at least one workflow support feature to the operator.

In an example, the camera configured to acquire 2D image data is located above the patient support.

FIG. 3 shows a medical image acquisition unit assistance method 200 in its basic steps. The method comprises in an acquiring step 210, acquiring by at least one camera at least one data of a human operator standing adjacent to a patient support of a medical image acquisition unit;

in a providing step 220, providing by the at least one camera the at least one data of the operator to a processing unit;

in a determining step 230, determining by the processing unit a height of the operator, wherein the determining comprises utilizing the at least one data; and in an outputting step 240, outputting by an output unit a signal to adjust a height of the patient support, wherein the adjustment comprises utilizing the height of the operator.

In an example, the utilizing the at least one data comprises determining a location of the operator in the at least one data.

In an example, the determining the height of the operator comprises determining at least one height at the determined location of the operator.

In an example, the at least one camera comprises a camera configured to acquire 2D image data, and the at least one data comprises a 2D image. The method can then comprise determining 225 by the processing unit the location of at least one body part of the operator in the 2D image.

In an example, the at least one camera comprises a camera configured to acquire depth or distance data, and the at least one data comprises depth or distance data. The method can then comprise determining by the processing unit the height of the operator on the basis of the depth or distance data at the determined location of the at least one body part of the operator.

In an example, the at least one body part of the operator comprises the top of the head of the operator and/or the neck of the operator and/or the shoulders of the operator.

In an example, the camera configured to acquire depth or distance data is located above the patient support.

In an example, determining the height of the operator comprises utilizing a known height of the camera configured to acquire depth or distance data above a floor upon which the patient support is located.

In an example, the depth or distance data comprises at least one distance between the camera and the at least one body part of the operator.

In an example, utilizing the at least one data comprises determining an identity of the operator in the at least one data.

In an example, determining the height of the operator comprises extracting the height of the operator from a database on the basis of the identity of the operator.

In an example, the at least one camera comprises a camera configured to acquire 2D image data, and the at least one data comprises a 2D image. The method can then comprise determining by the processing unit the identity of the operator comprising image analyzing the 2D image.

In an example, the method comprises determining by the processing unit at least one workflow support feature relating to operating the medical image acquisition unit by the operator comprising extracting the at least one workflow support feature from a database on the basis of the identity of the operator. The output unit then communicates the at least one workflow support feature to the operator.

In an example, the camera configured to acquire 2D image data is located above the patient support.

Thus, as described above a new technique for automatic height adjustment of the patient support to match the operator's height has been developed based on determining the operator's height, providing for faster and more convenient exam preparation. The new technique enables the provision of personalization features and support to operators that can account for their levels of experience and working styles through automatic identification of the operator.

An example uses, for example a ceiling-mounted image camera (such as an RGB camera—that need not be mounted on the ceiling) and a depth camera (that can be housed within the same camera body). A tailored body landmark detection model can be applied to the "RGB" image to locate key body parts of the operator, such as the head. The corresponding depth sensor can then be used to infer the operator's body height. This information is finally employed to automatically adjust the patient support height to allow for fast and convenient exam preparation.

Another example uses, for example the ceiling-mounted image camera (such as the RGB camera—that again need not be mounted on the ceiling). Automatic identification of the operator is enabled using the ceiling-mounted camera system. A dedicated network can be used for person detection in top-view images, as well as a person encoding convolutional neural network that can be used to create an encoded operator database. During inference, a database query is performed to automatically identify operators in the acquired camera images. This allows the height of the patient support to be adjusted to the height of the operator, and allows for intelligent personalization of other aspects of the workflow support system.

Thus, operators of different heights, and with different levels of experience and working styles can be accommodated.

The medical image acquisition unit assistance apparatus, the medical image acquisition unit assistance system, and the medical image acquisition unit assistance method are further explained in specific detail, where reference is made to FIGS. 4-7.

Figure 4:
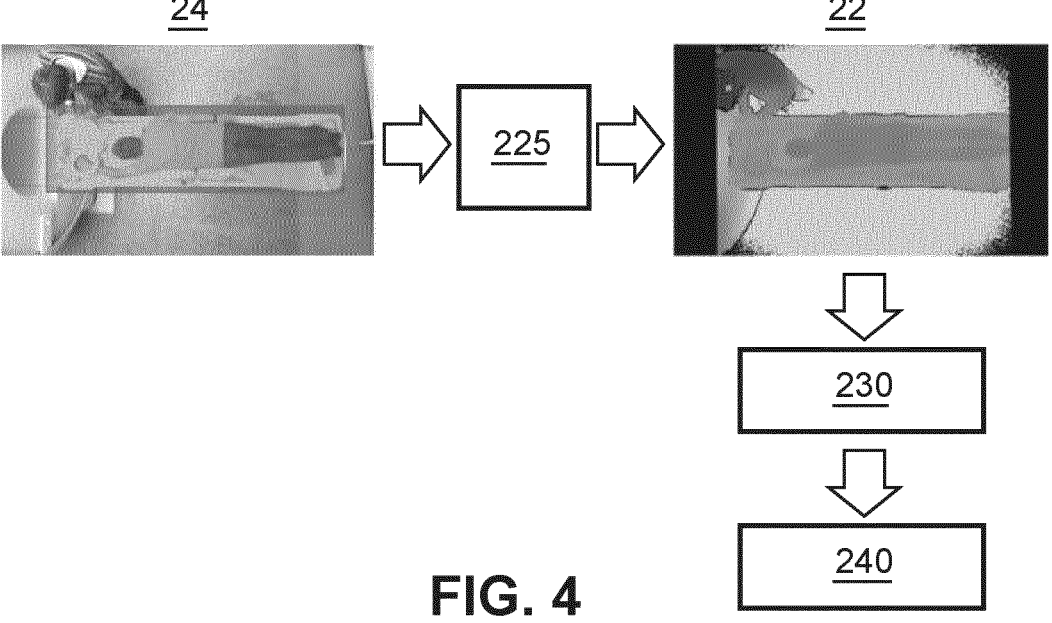
FIG. 4 shows pictorially an exemplar process of providing medical image acquisition unit assistance.

FIG. 4 shows pictorially an exemplar process of providing medical image acquisition unit assistance. A 2D image sensor such as a RGB sensor is indicated as 24, a depth sensor is indicated as 22. The image on the left has a border around the table indicating the table area that is excluded from network processing. The image on the left clearly shows the operator and their head. Head detection is indicated as 225, and the small circular marker as shown in the right hand image indicates where the operator's head as been determined or detected to be. Operator height estimation, as indicated as 230 is carried out, followed by table height adjustment, as indicated as 240.

Continuing with FIG. 4 the images produced by the camera's RGB sensor are first processed by a dedicated neural network that is trained to detect the operator's body landmarks. To account for the particular point of view of the camera, the network training can include a variety of top-view images of a large number of subjects. Creation of such a dataset can be realized in various ways, e.g. by combining/modifying publicly available data sources or by using the ceiling-mounted camera system itself. To avoid erroneous body height estimations due to the patient, the entire table area (marked by box around the table in FIG. 4) is excluded from the network processing by assigning a single value to all corresponding pixels.

In the implementation shown in FIG. 4, the network is trained to detect the operator's head. The image provided by the depth sensor is then evaluated at this location, providing an estimate of the distance between head and camera. By comparing this distance to the floor's depth value, the operator's body height can be estimated.

Thus, in summary the new technique consists of:

A ceiling-mounted RGB/Depth camera that provides a continuous data stream of the patient table.

There need not be a continuous stream of image data and other cameras than RGB cameras can be utilized, and the RGB camera and the depth camera need not be mounted on the ceiling.

A dedicated neural network is used for detection of body landmarks in the camera images.

Other image analysis techniques to that using a NN can be used to locate the operator's head.

An algorithm for operator identification and body height estimation is utilized.

The algorithm can be a simple subtraction of a distance of the depth camera to the top of the operator's head from a distance of the camera to the floor.

Many variations of this processing are possible:

Additional body landmarks can be used to infer body height, such as neck and shoulders.

Variation of the operator's body pose while working can be accounted for by using a dedicated estimation model that receives 3D landmark coordinates as input and produces body height estimates. Increasingly accurate estimates can be obtained by continuously processing the incoming RGB/Depth data stream and averaging the results.

Instead of a landmark detection model, a tailored person segmentation network can be used that provides an outline of the operator. An estimate of the operator's body height can then be obtained by taking the minimal depth value within the body outline.

To avoid incorrect table adjustments due to the patient, any images with more than one person in the non-table region can be excluded from the above-described processing (patients are usually accompanied by the operator to the patient support).

Once the operator's height is determined, the optimal table height is adjusted by the system. In a straightforward implementation, a simple linear model can be used for this purpose. More complex models that incorporate different body part sizes (length of legs, arms, torso) can be utilized.

In an even more advanced implementation, the table height is automatically adjusted during different phases of the exam preparation. As an example, if the patient height is known in advance, the height is adjusted such that the patient can comfortably get onto the table. Afterwards the table height is increased to create optimal working conditions for the operator.

Figure 5:
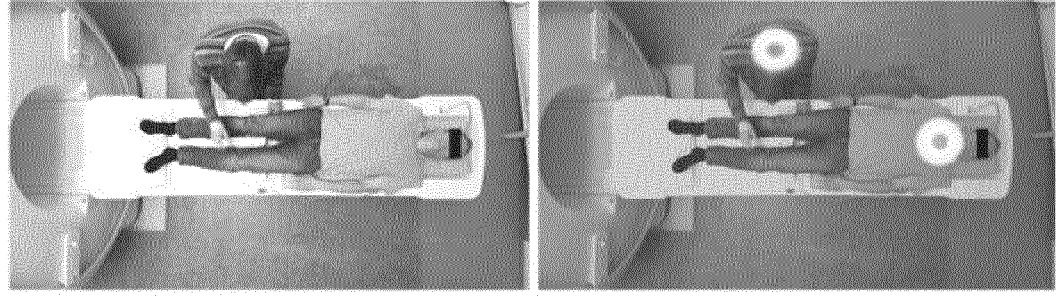
FIG. 5 shows an example of image acquisition and detection of the operator and patient within the image.
Figure 6:
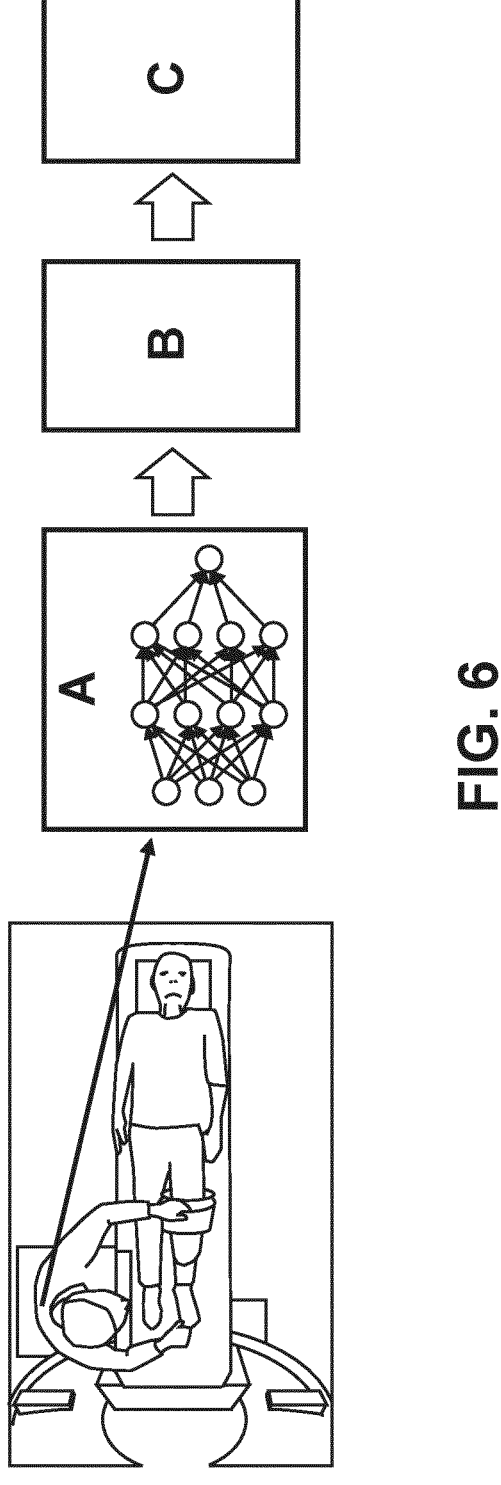
FIG. 6 shows pictorially a process of creating information that uniquely encodes the operator.
Figure 7:
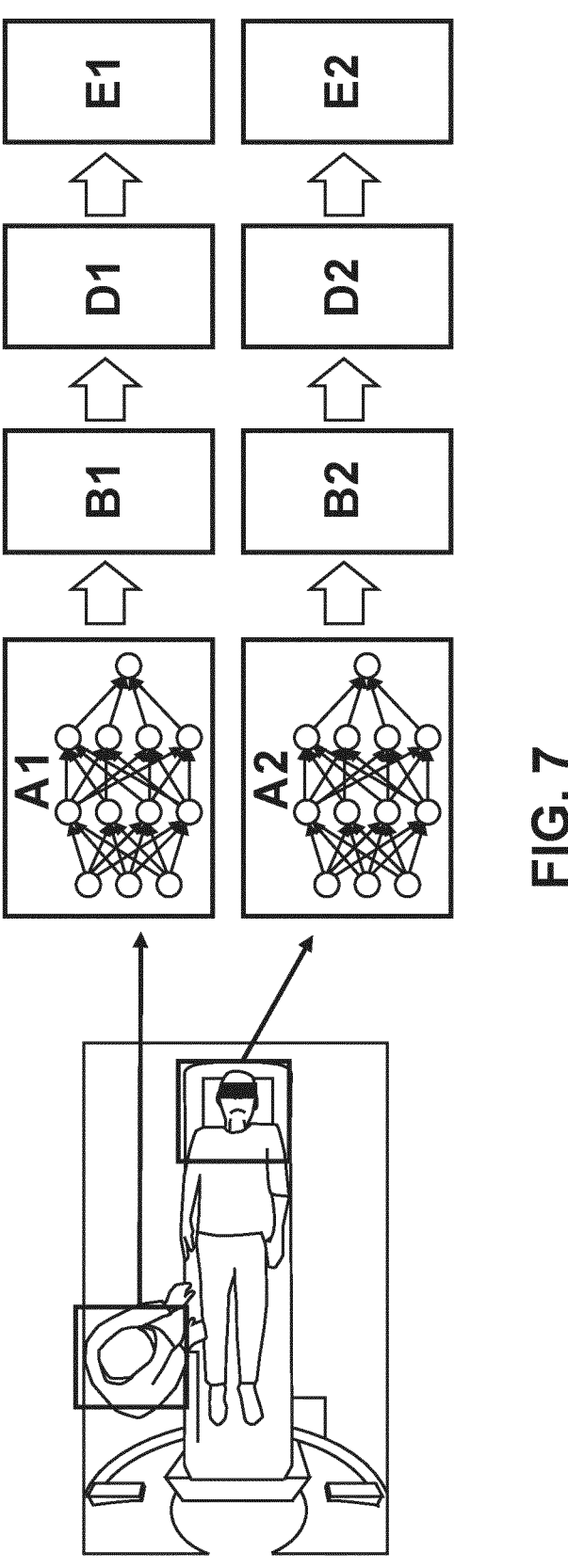
FIG. 7 shows pictorially a process of identifying an operator.

FIG. 4 relates to an example, where 2D imagery and depth data can be used to determine the height of the operator and enable the patient support (table) to be adjusted in height. FIGS. 5-7 then relate to an example, where the depth data is not required and the 2D imagery is utilized itself to enable the table height to be appropriately adjusted, and other support provided to the operator.

Regarding the example described with respect to FIGS. 5-7, the new technique consists of two main steps: database creation and operator identification during inference. These two steps can be separated in time, i.e. the database is created during a (silent) learning phase where operators at the given site are characterized, after which the algorithm is activated and personalization for all learned operators is realized. However, it is also possible to perform the two steps in an interleaved way: if an operator is detected, personalization features are activated if this person is found in the database; otherwise the operator is added to the database.

FIG. 5 shows on the left an example image acquired by a 2D image camera, such as the above described RGB camera, during preparation of a medical image examination, such as a MRI examination, and on the right is shown the output of the person detection network shown as an overlay.

FIG. 6 shows an exemplar workflow for creation of the operator database. The image region with the operator is cropped and processed by the person encoder, for example a CNN. A resultant feature vector F is stored in the database. A CNN encoder is represented by "A", at point "B" the feature vector F has been generated, and "C" represents the Operator database.

Database Creation

RGB images received by the ceiling-mounted camera device are automatically processed using a dedicated neural network for person detection. As detailed above, other 2D image formats can be utilized, and other machine learning algorithms other than a NN can be utilized, and the camera need not be mounted on the ceiling. To account for the particular point of view of the camera at the ceiling, the network training should include a variety of top-view images of a large number of subjects. Creation of such a dataset can be realized in various ways, e.g. by combining/ modifying publicly available data sources or by using the ceiling-mounted camera system itself. FIG. 5 shows an example of an image acquired by the camera during preparation of an MRI exam (left), as well as the output of the network as an overlay (right).

To safely identify the operator in such scenes, a number of criteria can be checked for all acquired images if required:
   Exactly two persons are detected
   One of these persons is located within the patient support area
   The second person is located outside of the patient support area
   If these criteria are fulfilled, the second person is identified as the operator.

Details of the database creation are shown in FIG. 6. The image region around the operator is cropped (100×100 pixels for example) and used as input to a dedicated person encoder CNN. The purpose of this network is to create a feature vector that uniquely encodes the detected operator.

To achieve such a behavior, a state-of-the-art CNN such as VGG [see for example: Simonyan, K. and Zisserman, A., 2014. Very deep convolutional networks for large-scale image recognition. arXiv preprint arXiv:1409.1556.] or Res-Net [see for example: He, K., Zhang, X., Ren, S. and Sun, J., 2016. Deep residual learning for image recognition. In Proceedings of the IEEE conference on computer vision and pattern recognition (pp. 770-778)] is trained for person re-identification, using a tailored loss function such as triplet loss [see for example: Hermans, A., Beyer, L. and Leibe. B., 2017. In defense of the triplet loss for person re-identification. arXiv preprint arXiv:1703.07737]. After training, instead of using the full CNN, the last fully connected layer (which produces the final output) is truncated, and the feature vector F that is produced by the second-last layer is used as a person encoding. It is to be noted that there are various other ways to obtain a person encoding with the desired properties.

The described processing is performed for all images of the camera's data stream, as long as the above-mentioned criteria are fulfilled, i.e. assuming that the operator can be clearly identified. By continuously processing camera data during a longer time period (say, several weeks), a comprehensive database of the operator staff is created. Well-known clustering algorithms like k-means clustering can be used to separate different operators within the database. Pruning or compression techniques can be applied to limit the database size, thereby improving performance during inference.

De-personalization of data is also provided, because since the person encoding is defined by the weights of the CNN, individual database entries cannot be re-identified as long as access to the CNN is restricted.

Inference: Operator Identification

Once the operator database has been created, the camera images that are acquired as part of the clinical routine are automatically analyzed, as shown exemplarily in FIG. 7. FIG. 7 shows an example of the workflow during inference. For each detected person, the corresponding image crop is processed by the person encoder CNN, and a database query for the resulting feature vector $F_1$ is performed to determine the person's identity (i.e., operator or patient), from which operator's height can be determined and the support table height adjusted and other personalized advice provided to the operator with respect to the exam. In FIG. 7 "A1" represents the "CNN encoder", "A2" represents the "CNN encoder", "B1" represented Feature vector $F_1$, "B2" represents Feature vector $F_2$, "D1" represents "Database query", "D2" represents "Database query", "E1" represents "Operator #1", and "E2" represents "Unknown (=patient)".

Continuing with FIG. 7, each camera image is first processed using the person detection network. For each detected person, the corresponding image region is cropped and processed by the person encoder CNN to obtain the associated feature vector $F_i$. If a similar feature vector is found in the database, the operator is identified accordingly. If no match is obtained, the person is considered unknown.

Personalization features for the camera-based workflow support system can be manually selected by the operators. Examples of adjustable features include:
   Operator height, and also the preferred height at which they want support tables to be positioned if necessary
   Coil placement guidance (e.g. don't show for certain coils)
   Restrict automatic iso-center determination to certain anatomies Visual or verbal warnings (collisions, body loops, etc.)

Automatic reminders for placement of nurse call, ear protection, etc.

Table speed

Table height at various time points (e.g., low table setting during table preparation and cleaning, higher table setting once patient is on the table)

Layout of touchscreen at the scanner

Thus, in summary, this example technique consists of the following:

A ceiling-mounted (or mounted elsewhere) RGB camera (or other 2D image camera) is used that provides a continuous data stream of the patient table (there need not be a continuous stream of data however and a single frame can be utilized).

A dedicated neural network (or other image processing algorithm) is used for person detection in the camera images.

A dedicated convolutional neural network (CNN) (or other encoder) is used for person encoding.

An algorithm is used for operator detection, creation of an operator database, and automatic operator identification during inference.

EMBODIMENTS

For the design and application of the new technique, additional embodiments can be considered:

Instead of manually selecting personalization features, operator preferences can be automatically learned based on the observed behavior. Examples include manually selected table height during different exam preparation phases, manual determination of iso-center location despite an available automated feature, ignored coil placement guidance, etc. Therefore, as described above an operator can be automatically detected and identified by the system. However, a new operator that is not yet present in the database triggers a routine of the software that automatically "learns" personalized system settings. This routine in effect tracks the operator's actions and interprets them as preferences. Such preferences can then be Manual selection of table height during various phases of the exam preparation can be stored and related to certain exam events: for example, very low table setting during cleaning, higher table setting during coil placement, etc.

Visual features such as coil placement guidance are manually enabled/disabled by the user.

If the visual layout of the display at the scanner touchscreen can be manually modified, these settings can be stored and brought up again automatically for the next exam.

If these manual selections are observed repeatedly for different exams, it is very likely that they correspond to operator preferences.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical image acquisition unit assistance apparatus, the apparatus comprising:

at least one camera disposed in a vicinity of a patient support of a medical image acquisition unit, and configured to: acquire at least one datum of a human operator standing adjacent to the patient support; and provide the at least one datum of the operator to a processor;

a non-transitory computer readable medium that stores a computer program element; and an output;

wherein when executed by the processor, the computer program element causes the processor to; determine a height of the operator, wherein the determination comprises utilization of the at least one datum, and wherein the utilization of the at least one datum comprises a determination of an identity of the operator in the at least one datum; and wherein the output is configured to output a signal to adjust a height of the patient support, wherein the adjustment comprises utilization of the height of the operator.

2. The medical image acquisition unit assistance apparatus of claim 1, wherein the utilization of the at least one datum comprises a determination of a location of the operator in the at least one datum.

3. The medical image acquisition unit assistance apparatus of claim 2, wherein the determination of the height of the operator comprises a determination of at least one height at the determined location of the operator.

4. The medical image acquisition unit assistance apparatus of claim 1, wherein the at least one camera comprises a camera configured to acquire 2D image data, wherein the at least one datum comprises a 2D image, and wherein the processor is configured to determine a location of at least one body part of the operator in the 2D image.

5. The medical image acquisition unit assistance apparatus of claim 4, wherein the at least one camera comprises a camera configured to acquire depth or distance datum, wherein the at least one datum comprises depth or distance data, and wherein the processor is configured to determine the height of the operator on a basis of the depth or distance data at the determined location of the at least one body part of the operator.

6. The medical image acquisition unit assistance apparatus of claim 5, wherein the at least one body part of the operator comprises a top of a head of the operator and/or a neck of an operator and/or shoulders of the operator.

7. The medical image acquisition unit assistance apparatus of claim 5, wherein the camera configured to acquire depth or distance data is configured to be located above the patient support.

8. The medical image acquisition unit assistance apparatus of claim 7, wherein the determination of the height of the operator comprises utilization of a known height of the camera configured to acquire depth or distance data above a floor upon which the patient support is located.

9. The medical image acquisition unit assistance apparatus of claim 1, wherein the determination of the height of the operator comprises an extraction of the height of the operator from a database on a basis of the identity of the operator.

10. The medical image acquisition unit assistance apparatus of claim 9, wherein the processor is configured to determine at least one workflow support feature relating to operation of the medical image acquisition unit by the operator comprising extraction of the at least one workflow support feature from a database on a basis of the identity of the operator, and wherein the output is configured to communicate the at least one workflow support feature to the operator.

11. The medical image acquisition unit assistance apparatus of claim 1, wherein the at least one camera comprises a camera configured to acquire 2D image data, wherein the at least one datum comprises a 2D image, and wherein the processor is configured to determine the identity of the operator comprising image analysis of the 2D image.

12. A medical image acquisition system comprising:

a medical image acquisition unit;

at least one camera disposed in a vicinity of a patient support of a medical image acquisition unit, and configured to: acquire at least one datum of a human operator standing adjacent to the patient support; and provide the at least one datum of the operator to a processor;

a computer readable medium that stores a computer program element; and an output;

wherein when executed by the processor, the computer program element causes the processor to:

determine a height of the operator, wherein the determination comprises utilization of the at least one datum, and wherein the utilization of the at least one datum comprises a determination of an identity of the operator in the at least one datum; and wherein the output is configured to output a signal to adjust a height of the patient support, wherein the adjustment comprises utilization of the height of the operator.

13. The medical image acquisition system of claim 12, wherein the utilization of the at least one datum comprises a determination of a location of the operator in the at least one datum.

14. The medical image acquisition system of claim 13, wherein the determination of the height of the operator comprises a determination of at least one height at the determined location of the operator.

15. The medical image acquisition system of claim 12, wherein the at least one camera comprises a camera configured to acquire 2D image datum, wherein the at least one datum comprises a 2D image, and wherein the processor is configured to determine a location of at least one body part of the operator in the 2D image.

16. The medical image acquisition system of claim 15, wherein the at least one camera comprises a camera configured to acquire depth or distance data, wherein the at least one datum comprises depth or distance data, and wherein the processor is configured to determine the height of the operator on a basis of the depth or distance data at the determined location of the at least one body part of the operator.

17. The medical image acquisition system of claim 16, wherein the at least one body part of the operator comprises a top of a head of the operator and/or a neck of an operator and/or shoulders of the operator.

18. A medical image acquisition unit assistance method, the method comprising:

acquiring by at least one camera at least one datum of a human operator standing adjacent to a patient support of a medical image acquisition unit;

providing by the at least one camera the at least one datum of the operator to a processor;

determining by the processor a height of the operator, wherein the determining comprises utilizing the at least one datum, and wherein utilizing the at least one datum comprises determining an identity of the operator in the at least one datum; and outputting by an output a signal to adjust a height of the patient support, wherein the adjustment comprises utilizing the height of the operator.

19. A computer program element for controlling the apparatus of claim 1, which when executed by a process is configured to perform a method comprising:

acquiring by at least one camera at least one datum of a human operator standing adjacent to a patient support of a medical image acquisition unit;

providing by the at least one camera the at least one datum of the operator to a processor;

determining by the processor a height of the operator, wherein the determining comprises utilizing the at least one datum, and wherein utilizing the at least one datum comprises determining an identity of the operator in the at least one datum; and outputting by an output a signal to adjust a height of the patient support, wherein the adjustment comprises utilizing the height of the operator.

20. A non-transitory computer readable medium having stored the computer program element according to claim 19.

\* \* \* \* \*